US008821870B2

(12) United States Patent
Robinson et al.

(10) Patent No.: US 8,821,870 B2
(45) Date of Patent: Sep. 2, 2014

(54) METHOD FOR TREATING ATROPHIC AGE RELATED MACULAR DEGENERATION

(75) Inventors: Michael R. Robinson, Irvine, CA (US); Wendy M. Blanda, Tustin, CA (US); Patrick M. Hughes, Aliso Viejo, CA (US); James A. Burke, Santa Ana, CA (US); Scott M. Whitcup, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/176,238

(22) Filed: Jul. 18, 2008

(65) Prior Publication Data

US 2010/0015158 A1     Jan. 21, 2010

(51) Int. Cl.
*A61K 39/395*     (2006.01)
*A61K 9/19*       (2006.01)
*A61K 9/48*       (2006.01)
*C07K 16/22*      (2006.01)

(52) U.S. Cl.
USPC ......... 424/133.1; 424/484; 424/489; 424/501

(58) Field of Classification Search
None
See application file for complete search history.

(56) References Cited

U.S. PATENT DOCUMENTS

| | | | |
|---|---|---|---|
| 5,264,188 A | 11/1993 | Lew | |
| 5,869,079 A | 2/1999 | Wong et al. | |
| 6,413,245 B1 | 7/2002 | Yaacobi et al. | |
| 7,090,681 B2 | 8/2006 | Weber et al. | |
| 2005/0244463 A1 | 11/2005 | Huang et al. | |
| 2005/0244464 A1 | 11/2005 | Hughes | |
| 2005/0244469 A1 | 11/2005 | Whitcup et al. | |
| 2005/0244471 A1 | 11/2005 | Shiah et al. | |
| 2005/0244506 A1 | 11/2005 | Burke et al. | |
| 2005/0250737 A1* | 11/2005 | Hughes et al. | 514/58 |
| 2005/0281861 A1 | 12/2005 | Hughes et al. | |
| 2006/0173060 A1 | 8/2006 | Change et al. | |
| 2006/0182771 A1* | 8/2006 | Dor et al. | 424/400 |
| 2006/0182781 A1 | 8/2006 | Hughes et al. | |
| 2006/0182783 A1* | 8/2006 | Hughes et al. | 424/427 |
| 2006/0233859 A1 | 10/2006 | Whitcup et al. | |
| 2006/0246145 A1 | 11/2006 | Change et al. | |
| 2007/0059336 A1 | 3/2007 | Hughes et al. | |
| 2007/0065444 A1* | 3/2007 | North et al. | 424/146.1 |
| 2007/0224246 A1 | 9/2007 | Hughes et al. | |
| 2008/0125377 A1* | 5/2008 | Bartels et al. | 514/23 |
| 2008/0131484 A1 | 6/2008 | Robinson et al. | |
| 2008/0268051 A1 | 10/2008 | Hughes et al. | |
| 2011/0034448 A1 | 2/2011 | Chang et al. | |

FOREIGN PATENT DOCUMENTS

| | | |
|---|---|---|
| EP | 0488401 A1 | 3/1992 |
| EP | 430539 | 10/1994 |
| WO | 2005046641 A2 | 5/2005 |
| WO | WO2005/110436 | 11/2005 |
| WO | 2007128526 A2 | 11/2007 |
| WO | 2007130134 A2 | 11/2007 |
| WO | WO 2007/130134 | 11/2007 |
| WO | 2008063932 A2 | 5/2008 |

OTHER PUBLICATIONS

Zhu et al, Investigational New Drugs 17: 195-212, 1999.*
Webster's II New Riverside University Dictionary, p. 933, 1984.*
Petrukhin et al, Expert Opin Ther Target 11(5): 625-639, 2007.*
Ngo et al., The Protein Folding Problem and Tertiary Structure Prediction, pp. 491-495, 1994.*
Stryer et al, in Biochemistry, Third edition, W H Freeman Company, New York, pp. 31-33, 1998.*
Chiou, George C.Y., "Pharmacological treatment of dry age-related macular degeneration (AMD)", Taiwan Journal of Ophthalmology 1 (2011) 2-5.
Gehrs et al, "Age-related macular degeneration-emerging pathogenic and therapeutic concepts", Ann Med 2006; 38: 450-471.
Krzystolik et al. (2002) "Prevention of experimental choroidal neovascularization with intravitreal anti-vascular endothelial growth factor antibody fragment" *Arch. Ophthalmol.* 120: 338-346.
Kuno et al, "Dry Age-Related Macular Degeneration: Recent Progress of Therapeutic approaches", Current Molecular Pharmaology, 2011, 4, 196-232.
Pe'er et al, "Vascular Endothelial Growth Factor Upregulation in Human Central Retinal Vein Occlusion", Ophthalmology 1998; 105: 412-416.
Shen et al, "Preclinical Evaluation of a Phosphorothioate Oligonucleotide in the Retina of *Rhesus Monkey*", Laboratory Investigation, 2002, vol. 82, No. 2, 167-182.
U.S. Appl. No. 60/567,423, filed Apr. 30, 2004.
U.S. Appl. No. 60/721,600, filed Sep. 28, 2005.
U.S. Appl. No. 11/116,698, filed Apr. 30, 2004.
U.S. Appl. No. 11/364,687, filed Feb. 27, 2006.
U.S. Appl. No. 11/370,301, filed Mar. 8, 2006.
U.S. Appl. No. 11/565,917, filed Dec. 1, 2006.
U.S. Appl. No. 11/742,350, filed Apr. 30, 2007.
U.S. Appl. No. 11/859,310, filed Sep. 21, 2007.
U.S. Appl. No. 11/952,938, filed Dec. 7, 2007.
Aiello et al, "Vascular Endothelial Growth Factor in Ocular Fluid of Patients with Diabetic Retinopathy and Other Retinal Disorders", The New England Journal of Medicine, Dec. 1, 1994, pp. 1480-1487.
Yehoshua et al. (2011) "Current clinical trials in dry AMD and the definition of appropriate clinical outcome measures" *Seminars in Opthalmology* 26(3): pp. 167-180.
Lee et al, "Drug Delivery to the posterior segment", Retina, 1989, Chapter 25, pp. 483-498.
Lin et al, "Vascular Endothelial Growth Factor Gene Polymorphisms in Age-Related Macular Degeneration", Am. J. Ophthalmol. Mar. 29, 2008, pp. 1045-1051.
Maurice, D.M., "Micropharmaceutics of the eye", Ocular Inflammation Ther., 1983, 1: pp. 97-102.

(Continued)

*Primary Examiner* — Phuong Huynh

(74) *Attorney, Agent, or Firm* — Jennifer C. Cheng

(57) ABSTRACT

Compositions and methods for treating dry age related macular degeneration (dry AMD) by administration to an intraocular location of an anti-neovascular agent (such as bevacizumab) in either a liquid or solid polymeric vehicle (or both), such as a biodegradable hyaluronic acid or PLGA (or PLA).

4 Claims, 1 Drawing Sheet

(56) References Cited

OTHER PUBLICATIONS

Dunn K. et al., *ARPE-19, a human retinal pigment epithelial cell line with differentiated properties*, Exp Eye Res. Feb. 1996, 62: 155-169.

Heller, *Biodegradable Polymers in Controlled Drug Delivery*, In: "CRC Critical Reviews in Therapeutic Drug Carrier Systems", vol. 1. CRC Press, Boca Raton, FL (1987), 1 (1) : 39-90.

Cook H., et al., *Age-related macular degeneration: diagnosis and management*, Br Med Bull. 2008;85:127-49.

Lin J., et al., *Vascular Endothelial Growth Factor Gene Polymorphisms in Age-related Macular Degeneration*, Am J Ophthalmol. Mar. 29, 2008.

Olsen, T.W. et al. (1995), *Human scleral permeability: effects of age, cryotherapy, transscleral diode laser, and surgical thinning*, Invest. Ophthalmol. Vis. Sci. 36:1893-1903.

Maurice, D.M. (1983) *Micropharmaceutics of the eye*, Ocular Inflammation Ther. 1:97-102; Lee, V.H.L. et al. (1989).

Asbell P.A., et al Effects of topical antiglaucoma medications on the ocular surface, Ocul Surf Jan. 2005;3(1):27-40.

Mueller M., et al. Tear film break up time and Schirmer test after different antiglaucomatous medications, Invest Ophthalmol Vis Sci Mar. 15, 2000;41(4):S283.

Cook H L et al: "Age-related macular degeneration: diagnosis and management" British Medical Bulletin, vol. 85, Mar. 2008, pp. 127-149, XP002568505 ISSN: 0007-1420, the whole document.

International Search Report, PCT/US2009/050373, May 3, 2010.

\* cited by examiner

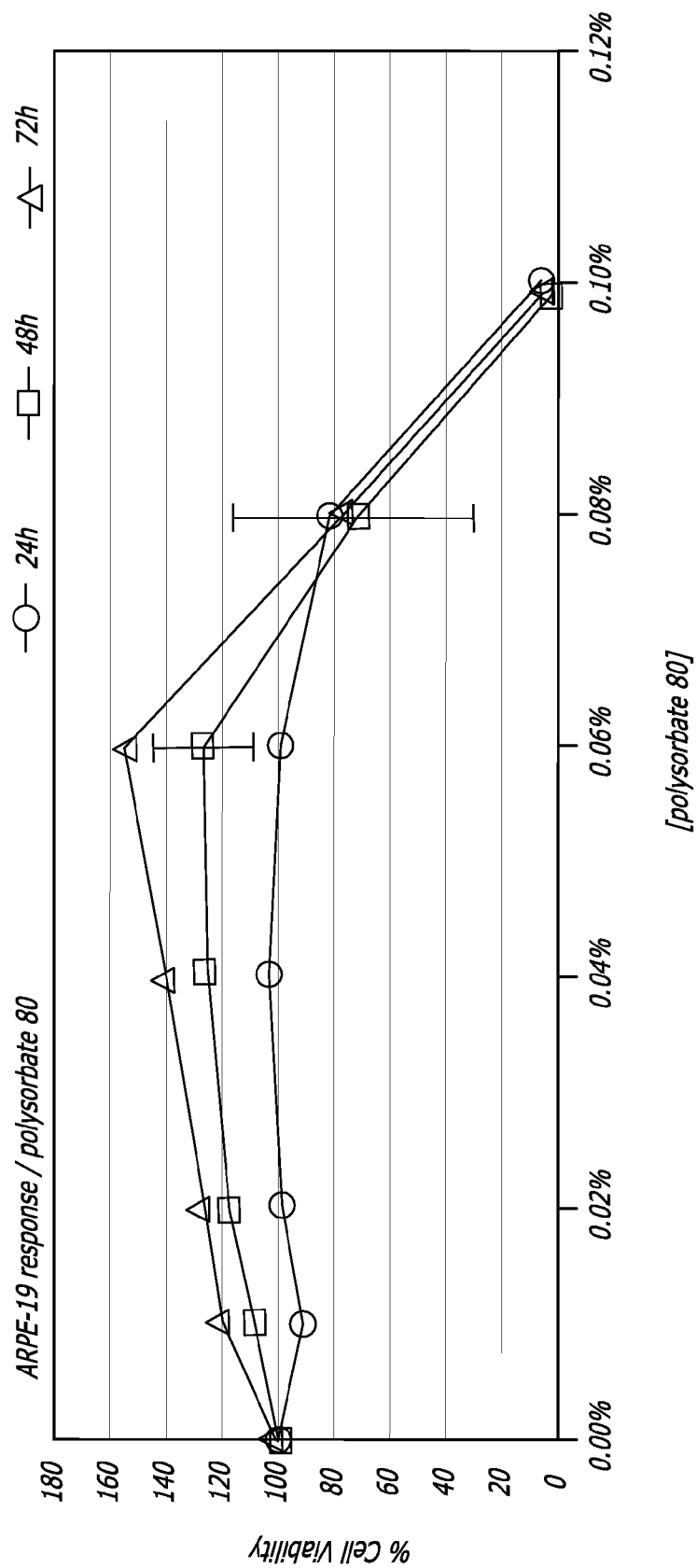

METHOD FOR TREATING ATROPHIC AGE RELATED MACULAR DEGENERATION

BACKGROUND

The present invention is directed to compositions (i.e. drug delivery systems) and methods for treating ocular conditions, and for preventing the occurrence of certain ocular conditions. In particular the present invention is directed to pharmaceutical compositions and methods for treating and for preventing posterior ocular conditions, for example by preventing retinal, choroidal and/or macular neovascularizations and/or for treating various types of macular degeneration (such as age related macular degeneration), by use of a drug delivery system comprising an anti-neovascular agent.

In the industrialized world the average life expectancy is over 80 years of age and is increasing steadily. Unfortunately, the quality of life for the elderly is often dramatically decreased by the ocular condition known as age related macular degeneration ("ARMD" or "AMD"). AMD is the leading cause of blindness worldwide and the World Health Organization has estimated that about 14 million people are blind or severely impaired because of AMD. The affliction of AMD has great impact on the physical and mental health of the geriatric population and their families and presents a significant public health care burden. The seminal characteristic of AMD is progressive loss of central vision attributable to degenerative and neovascular changes in the macula, a specialized area in the center of the retina.

There are two forms of AMD, atrophic or dry AMD and neovascular or wet AMD. Typically AMD begins as dry AMD. Dry AMD is characterized by the formation of yellow plaque like deposits called drusen in the macula, between the retinal pigment epithelium (RPE) and the underlying choroid. About 15% of dry AMD patients develop wet AMD which is characterized by choroidal neovascularization, that is by the formation of new blood vessels in the choroid, and vision loss.

While there is no cure for AMD there are known treatments for wet AMD (the less prevalent form of AMD), such as the use of anti-neovascular agents and photodynamic therapy (laser irradiation of the macula). Anti-neovascular agents for treatment of wet AMD include agents which block the action of vascular endothelial growth factor (VEGF) thereby slowing angiogenesis (formation of new blood vessels in the retina) which leads to choroidal neovascularization and loss of vision in wet AMD patients. Such "anti-VEGF" agents approved or in clinical study for treating wet AMD include bevacizumab (AVASTIN™), ranibizumab (LUCENTIS™), and pegaptanib (MACUGEN™). Bevacizumab is a full-length anti-VEGF antibody approved for use in metastatic colon cancer. Ranibizumab is a humanized anti-VEGF monoclonal antibody fragment that inhibits all isotypes of VEGF and pegaptanib is a VEGF-neutralizing aptamer that specifically inhibits one isoform of VEGF (VEGF-165).

Other known anti-VEGF agents include small interfering RNA (siRNAs); corticosteroids such as anacortave acetate, triamcinolone acetonide and fluocinolone acetonide; receptor tyrosine kinase inhibitors (such as vatalanib and Ruboxistaurin [decreases protein kinase C activity]); squalamine lactate, and; growth factors, including pigment epithelium-derived factor. siRNAs can inhibit VEGF production and VEGF receptor production, corticosteroids can treat the DME aspect of wet AMD, receptor tyrosine kinase inhibitors inhibit downstream effects of VEGF, and squalamine lactate inhibits plasma membrane ion channels with downstream effects on VEGF.

An ocular condition can include a disease, aliment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball. A front of the eye or anterior ocular condition is a disease, ailment or condition which affects or which involves an ocular region or site, such as a periocular muscle, an eye lid or an eye ball tissue or fluid which is located anterior to the posterior wall of the lens capsule or ciliary muscles. Thus, a front of the eye ocular condition primarily affects or involves, the conjunctiva, the cornea, the conjunctiva, the anterior chamber, the iris, the posterior chamber (behind the iris but in front of the posterior wall of the lens capsule), the lens and the lens capsule as well as blood vessels, lymphatics and nerves which vascularize, maintain or innervate an anterior ocular region or site.

A front of the eye (anterior) ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can be considered to be a front of the eye ocular condition because a clinical goal of glaucoma treatment can be to reduce a hypertension of aqueous fluid in the anterior chamber of the eye (i.e. reduce intraocular pressure).

A posterior (or back of the eye) ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, macular degeneration (such as non-exudative age related macular degeneration and exudative age related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitic retinal disease; retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can also be considered a posterior ocular condition because a therapeutic goal of glaucoma treatment is to prevent the loss of or reduce the occurrence of loss of vision due to damage to or loss of retinal cells or optic nerve cells (i.e. neuroprotection).

As stated macular degeneration, such as AMD is a leading cause of blindness in the world and it is estimated that thirteen million Americans have evidence of macular degeneration. Macular degeneration results in a break down the macula, the light-sensitive part of the retina responsible for the sharp, direct vision needed to read or drive. Central vision is especially affected. Macular degeneration is diagnosed as either dry (atrophic) or wet (exudative). The dry form of macular degeneration is more common than the wet form of macular degeneration, with about 90% of AMD patients being diagnosed with dry AMD. The wet form of the disease usually leads to more serious vision loss. Macular degeneration can produce a slow or sudden painless loss of vision. The cause of macular degeneration is not clear. The dry form of AMD may result from the aging and thinning of macular tissues, depositing of pigment in the macula, or a combination of the two processes. With wet AMD, new blood vessels grow beneath the retina and leak blood and fluid. This leakage causes retinal cells to die and creates blind spots in central vision.

Macular edema ("ME") can result in a swelling of the macula. The edema is caused by fluid leaking from retinal blood vessels. Blood leaks out of the weak vessel walls into a very small area of the macula which is rich in cones, the nerve endings that detect color and from which daytime vision depends. Blurring then occurs in the middle or just to the side of the central visual field. Visual loss can progress over a period of months. Retinal blood vessel obstruction, eye inflammation, and age-related macular degeneration have all been associated with macular edema. The macula may also be affected by swelling following cataract extraction. Symptoms of ME include blurred central vision, distorted vision, vision tinted pink and light sensitivity. Causes of ME can include retinal vein occlusion, macular degeneration, diabetic macular leakage, eye inflammation, idiopathic central serous chorioretinopathy, anterior or posterior uveitis, pars planitis, retinitis pigmentosa, radiation retinopathy, posterior vitreous detachment, epiretinal membrane formation, idiopathic juxtafoveal retinal telangiectasia, Nd:YAG capsulotomy or iridotomy. Some patients with ME may have a history of use of topical epinephrine or prostaglandin analogs for glaucoma. The first line of treatment for ME is typically anti-inflammatory drops topically applied. The increase in retinal capillary permeability and subsequent retinal edema of macula edema can ensue from of a breakdown of the blood retina barrier mediated in part by vascular endothelial growth factor (VEGF), a 45 kD glycoprotein. It is known that VEGF can increase vascular permeability; possibly by increasing phosphorylation of tight junction proteins such as occludin and zonula occluden. Similarly, in human non-ocular disease states such as ascites, VEGF has been characterized as a potent vascular permeability factor (VPF).

Biochemically, VEGF is known to be a major contributor to the increase in the number of capillaries in tissue undergoing angiogenesis. Bovine capillary endothelial cells will proliferate and show signs of tube structures in vitro upon stimulation by VEGF. Upregulation of VEGF is a major component of the physiological response to exercise and its role in angiogenesis is suspected to be a possible treatment in vascular injuries.

VEGF causes an intracellular signaling cascade in endothelial cells. VEGF binding to VEGF receptor-2 (VEGFR-2) initiates a tyrosine kinase signaling cascade that stimulates the production of factors that variously stimulate vessel permeability (epithelial nitric oxide synthase; (eNOS), proliferation/survival (bFGF; basic fibroblast growth factor), migration (intercellular adhesion molecules (ICAMs); vascular cell adhesion molecules (VCAMs); matrix metalloproteases (MMPs)) and finally differentiation into mature blood vessels. As part of the angiogenic signaling cascade, NO (nitric oxide) is widely considered to be a major contributor to the angiogenic response because inhibition of NO significantly reduces the effects of angiogenic growth factors.

The normal human retina contains little or no VEGF; however, hypoxia causes upregulation of VEGF production. Disease states characterized by hypoxia-induced VEGF upregulation include, without limitation, CRVO and BRVO. This hypoxia induced upregulation of VEGF can be inhibited pharmacologically. Pe'er J. et al., *Vascular Endothelial Growth Factor Upregulation In Human Central Retinal Vein Occlusion*, OPHTHALMOLOGY 1998; 105:412-416. It has been demonstrated that anti-VEGF antibodies can inhibit VEGF driven capillary endothelial cell proliferation. Thus, attenuation of the effects of VEGF introduces a rationale for treatment of macular edema from venous occlusive disease.

Additionally, over expression of VEGF causes increased permeability in blood vessels in addition to stimulating angiogenesis. In "wet" or exudative macular degeneration, VEGF causes proliferation of capillaries into the retina. Since the increase in angiogenesis also causes edema, blood and other retinal fluids leak into the retina causing loss of vision. Our invention includes a novel treatment for macular degeneration without neovascularization by use of an anti-neovascular agent, such as a VEGF inhibiting aptamer, or other VEGF-inhibiting compound, such as a to stop the main signaling cascade for angiogenesis, thereby preventing these symptoms.

Diabetic retinopathy is the leading cause of blindness among adults aged 20 to 74 years. Macular ischemia is a major cause of irreversible vision acuity loss and decreased contrast sensitivity in patients with diabetic retinopathy. The capillary nonperfusion and decreased capillary blood flow that is responsible for this ischemia is seen clinically on the fluorescein angiogram as an increase in the foveal avascular zone (FAZ) or an irregularity of the outline of the FAZ. These findings are predictors of the other, perhaps more well-known, sight-threatening complications of diabetic retinopathy, including macular edema and proliferative retinopathy. Perhaps more importantly, extensive capillary nonperfusion is also a predictor of a poor visual prognosis from diabetic retinopathy.

There are treatments available or in development for macular edema and proliferative retinopathy, such as laser photocoagulation, intravitreal corticosteroids and anti-VEGF therapies. Although laser photocoagulation has been studied for vision loss directly associated with macular ischemia, there is currently no known treatment for this indication.

The exterior surface of the normal globe mammalian eye has a layer of tissue known as conjunctival epithelium, under which is a layer of tissue called Tenon's fascia (also called conjunctival stroma). The extent of the Tenon's fascia extending backwards across the globe forms a fascial sheath known as Tenon's capsule. Under Tenon's fascia is the episclera. Collectively, the conjunctival epithelium and the Tenon's fascia is referred to as the conjunctiva. As noted, under Tenon's fascia is the episclera, underneath which lies the sclera, followed by the choroid. Most of the lymphatic vessels and their associated drainage system, which is very efficient at removing therapeutic agents placed in their vicinity, is present in the conjunctiva of the eye.

A therapeutic agent can be administered to the eye to treat an ocular condition. For example the target tissue for an antihypertensive therapeutic agent to treat the elevated intraocular pressure characteristic of glaucoma can be the ciliary body and/or the trabecular meshwork. Unfortunately, administration of an ocular topical antihypertensive pharmaceutical in the form of eye drops can result in a rapid wash out of most if not all of the therapeutic agent before it reaches the ciliary body and/or the trabecular meshwork target tissue, thereby requiring frequent redosing to effectively treat a hypertensive condition. Additionally, side effects to patients from topical administration of antiglaucoma medications and their preservatives range from ocular discomfort to sight-threatening alterations of the ocular surface, including conjunctival hyperemia (eye redness), stinging, pain, decreased tear production and function, decreased tear film stability, superficial punctate keratitis, squamous cell metaplasia, and changes in cell morphology. These adverse effects of topical antiglaucoma eyedrops can interfere with the treatment of glaucoma by discouraging patient dosing compliance, and as well long-term treatment with eyedrops is associated with a higher failure of filtration surgery. Asbell P. A., et al *Effects of topical antiglaucoma medications on the ocular surface*, Ocul Surf January 2005;3(1):27-40; Mueller M., et al. *Tear film break up time and Schirmer test after different antiglaucomatous medications*, Invest Ophthalmol Vis Sci Mar. 15, 2000;41(4):S283.

It is known to administer a drug depot to the posterior (i.e. near the macula) sub-Tenon space. See eg column 4 of U.S. Pat. No. 6,413,245. Additionally, it is known to administer a polylactic implant to the sub-tenon space or to a suprachoroidal location. See eg published U.S. Pat. No. 5,264,188 and published U.S. patent application 20050244463

An anti-neovascular agent can be used for the treatment of an ocular condition, such as a posterior ocular condition, which involves angiogenesis such as choroidal neovascularization ("CNV"). Delivery to the eye of a therapeutic amount of an anti-neovascular agent (a drug) can be difficult, if not impossible, for drugs with short plasma half-lives since the exposure of the drug to intraocular tissues is limited. Therefore, a more efficient way of delivering a drug to treat a posterior ocular condition, such as CNV, is to place the drug directly in the eye, such as directly into the vitreous. Maurice, D. M. (1983) *Micropharmaceutics of the eye*, Ocular Inflammation Ther. 1:97-102; Lee, V. H. L. et al. (1989), *Drug delivery to the posterior segment" Chapter* 25 In Retina. T. E. Ogden and A. P. Schachat eds., St. Louis: C V Mosby, Vol. 1, pp. 483-98; and Olsen, T. W. et al. (1995), *Human scleral permeablilty: effects of age, cryotherapy, transscleral diode laser, and surgical thinning*, Invest. Ophthalmol. Vis. Sci. 36:1893-1903.

Techniques such as intravitreal injection of a drug have shown promising results, but due to the short intraocular half-life of active agent, including anti-neovascular agents, intravitreal injections must be frequently repeated to maintain a therapeutic drug level. In turn, this repetitive process increases the potential for side effects such as infection, retinal detachment, endophthalmitis, and cataract.

An intraocular drug delivery system can be made of a biodegradable polymer such as a poly(lactide) (PLA) polymers, poly(lactide-co-glycolide) (PLGA) polymers, as well as copolymers of PLA and PLGA polymers. PLA and PLGA polymers degrade by hydrolysis, and the degradation products, lactic acid and glycolic acid, are metabolized into carbon dioxide and water.

Drug delivery systems have been formulated with various active agents. For example, it is known to make 2-methoxyestradiol poly lactic acid polymer implants (as rods and wafers), intended for intraocular use, by a melt extrusion method. See eg published U.S. patent application 20050244471. Additionally, it is known to make brimonidine poly lactic acid polymer implants and microspheres intended for intraocular use. See eg published U.S. patent applications 20050244463 and 20050244506, and U.S. patent application Ser. No. 11/395,019. Furthermore, it is known to make bimatoprost containing polylactic acid polymer implants and microspheres intended for intraocular use. See eg published U.S. patent applications 2005 0244464 and 2006 0182781, and U.S. patent applications Ser. Nos. 11/303,462, and; 11/371,118.

EP 488 401 discusses intraocular implants, made of certain polylactic acids, to be applied to the interior of the eye after a surgical operation for disorders of the retina/vitreous body or for glaucoma. EP 430539 discusses use of a bioerodible implant which is inserted in the suprachoroid.

U.S. application Ser. No. 11/565,917 filed Dec. 1, 2006 discloses intraocular (including sub-tenon's) administration of various solid, drug-containing implants.

Intraocular drug delivery systems which are sutured or fixed in place are known. Suturing or other fixation means requires sensitive ocular tissues to be in contact with aspects of a drug delivery system which are not required in order to contain a therapeutic agent within or on the drug delivery system or to permit the therapeutic agent to be released in vivo. As such suturing or eye fixation means a merely peripheral or ancillary value and their use can increase healing time, patient discomfort and the risk of infection or other complications.

U.S. patent applications Ser. Nos. 11/742,350; 11/859,310; 11/952,938; 11/364,687 discuss use of intraocular compositions comprising anti-VEGF therapeutic agent, such as bevacizumab. Formulations of macromolecules for intraocular use are known, See eg applications Ser. Nos. 11/370,301; 11/364,687; 60/721,600; 11/116,698 and 60/567,423.

Significantly, although dry AMD is the most common form of AMD, except for use of anti-oxidants (such as high dose vitamins C, E, beta carotene and/or zinc to neutralize reactive oxygen species in the retina) "there are no current therapies for the more common 'dry' AMD". Gehrs K., et al., *Age-related macular degeneration—emerging pathogenetic and therapeutic concepts*, Ann Med 2006; 38: 450-471. Thus, "there is no effective treatment for the most prevalent atrophic (dry) form of AMD". Petrukhin, K., *New therapeutic targets in atrophic age-related macular degeneration*, Expert Opin. Ther. Targets 92007) 11(5): 625-639.

Thus it would be advantageous to have a sustained release drug delivery system suitable for intraocular use for treatment of dry AMD. What is needed therefore is a composition and method for treating dry AMD.

SUMMARY

The present invention fulfills this need by providing compositions and methods for treating dry AMD. In particular the present invention provides an effective intraocular therapy for treating dry AMD by use of a sustained release drug delivery system suitable for intraocular (i.e. intravitreal) use.

Definitions

The terms below are defined to have the following meanings:

"Anti-neovascular agent" means a compound which has an anti-angiogenic effect when administered to an eye such as by intravitreal injection or implantation.

"Anti-VEGF agent" means a compound which inhibits an activity or an effect of VEGF, and includes bevacizumab, ranibizumab, pegaptanib, VEGF-neutralising aptamers, anti-VEGF monoclonal antibodies, siRNAs, corticosteroids such as anacortave acetate, triamcinolone acetonide and fluocinolone acetonide; receptor tyrosine kinase inhibitors, such as vatalanib and Ruboxistaurin, squalamine lactate, and; growth factors, including pigment epithelium-derived factor.

"About" means approximately or nearly and in the context of a numerical value or range set forth herein means ±10% of the numerical value or range recited or claimed.

"Active agent", "drug" and "therapeutic agent" are used interchangeably herein and refer to any substance (including a biologic or macromolecule) used to treat an ocular condition.

"Biocompatible" with regard to a drug delivery system means that upon intraocular administration of the drug delivery system to a mammalian eye a significant immunogenic reaction does not occur.

"Bioerodible polymer" means a polymer which degrades in vivo. The polymer can be a gel or hydrogel type polymer, PLA or PLGA polymer or mixtures or derivatives thereof. The words "bioerodible" and "biodegradable" are synonymous and are used interchangeably herein.

"Drug delivery system" means a liquid, gel, hydrogel, high viscosity formulation, solid implant or microspheres from which a therapeutic amount of a therapeutic agent can be released upon in vivo administration of the drug delivery system, without any requirement that the drug delivery system by sutured to ocular tissue or otherwise fixed in place by an attachment means.

"Dry AMD" (also referred to as atrophic age related macular degeneration) means a human retinal condition in which drusen are present in the macula but with little or no retinal neovascularization. Dry AMD includes category 1 AMD (few or only small drusen present), category 2 AMD (early AMD in which with small to moderate size drusen are present) and category 3 AMD (intermediate AMD is which numerous medium or large drusen are present). Contrarily, "wet AMD" means a human retinal condition characterized by the presence of retinal neovascularization (category 4 or advanced AMD) or vision loss. Small drusen has a diameter less than 63 microns, medium size drusen has a diameter between 63 to 124 microns, and large drusen has diameter of 125 microns or more.

"Intraocular" means within or under an ocular tissue. An Intraocular administration of a drug delivery system includes administration of the drug delivery system to a sub-Tenon, subconjunctival, suprachoroidal, intravitreal and like locations. An intraocular administration of a drug delivery system excludes administration of the drug delivery system to a topical, systemic, intramuscular, subcutaneous, intraperitoneal, and the like location.

"Ocular condition" means a disease, aliment or condition which affects or involves the eye or one or the parts or regions of the eye, such as a retinal disease. The eye includes the eyeball and the tissues and fluids which constitute the eyeball, the periocular muscles (such as the oblique and rectus muscles) and the portion of the optic nerve which is within or adjacent to the eyeball.

"Posterior ocular condition" means a disease, aliment or condition which affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerve which vascularize or innervate a posterior ocular region or site.

"Substantially" means between 51% to 100% of the item or amount so qualified.

"Suitable for insertion (or implantation) in (or into) an ocular region or site" with regard to a drug delivery system, means a drug delivery system which has a size (dimensions) such that it can be administered, injected, inserted or implanted without causing excessive tissue damage and without unduly physically interfering with the existing vision of the patient into which the implant is implanted or inserted.

"Sustained" as in "sustained period" or "sustained release" means for a period of time greater than three days, preferably for at least 20 days (i.e. for a period of time from 20 days to 365 days), and most preferably for at least 30 days. A sustained release can persist for between about two months and about a four months.

"Therapeutic levels" or "therapeutic amount" means an amount or a concentration of an active agent that has been locally delivered to an ocular region that is appropriate to safely treat an ocular condition so as to reduce or prevent a symptom of an ocular condition.

"Treating" means to administer a treatment to a human patient. Treating includes a treatment which acts to reduce an existing clinical symptom (such as the amount or extent of drusen present) of a present, diagnosed ocular condition (such as dry AMD), as well as prevention of deterioration of (or slowing of the rate of deterioration of) the present, diagnosed ocular condition to another ocular condition (such as wet AMD) which has additional or new clinical symptoms (such as vision loss and/or neovascularization).

An embodiment of our invention is a method for treating a retinal disease, such as macular degeneration, such as dry age related macular degeneration (dry AMD). The method can comprise the step of administering an anti-neovascular agent to an eye of a patient with dry AMD, thereby treating the dry AMD. The anti-neovascular agent can be an anti-vascular endothelial growth factor (VEGF) agent and exemplary anti-VEGF agent can be bevacizumab, ranibizumab and pegaptanib, as well as derivatives, esters, salts and mixtures of these anti-VEGF agents thereof.

Preferably, the anti-neovascular agent is administered in a method within the scope of our invention as or as part of a biocompatible drug delivery system. Thus, the biocompatible drug delivery system can comprise the anti-neovascular agent and a polymeric vehicle associated with the anti-neovascular agent. The polymeric vehicle can be selected from the group consisting of a polymeric lactic acid ("PLA), a polymeric glycolic acid, a lactic acid-glycolic acid co-polymer ("PLGA"), a polymeric hydroxypropylmethylcellulose, and a polymeric hyaluronic acid, and mixtures thereof.

The anti-neovascular agent can be associated with the polymeric vehicle by being dispersed homogenously throughout the polymeric vehicle and the administering step of the method can be carried out by injecting the anti-neovascular agent to an anterior intraocular location or to a posterior intraocular location, such as into the vitreous cavity.

A further embodiment of our invention is a method for treating dry AMD by preparing a biocompatible drug delivery system comprising an anti-neovascular agent (i.e. bevacizumab or a derivative, ester, or salt thereof) and a polymeric vehicle associated with the anti-neovascular agent, and injecting the drug delivery system into the vitreous cavity of the eye of a patient with dry AMD, thereby treating the dry AMD.

Preferably, a drug delivery system within the scope of our invention can contain or comprise from about 5 µg to about 3 mg of an anti-neovascular agent, bevacizumab. Stated somewhat differently, drug delivery system within the scope of our invention can release in vivo an average of between about 10 ng to about 40 µg of an anti-neovascular agent (such as bevacizumab) over a 24 hour period after intraocular injection of implantation of the drug delivery system. Preferably, the drug delivery system releases an average of between about 14 µg to about 28 µg of the anti-neovascular agent (i.e. bevacizumab) over a 24 hour period after intraocular injection of implantation of the drug delivery system. More preferably, the drug delivery system can release an average of between about 7 µg to about 14 µg of the anti-neovascular agent (i.e. bevacizumab) over a 24 hour period after intraocular injection of implantation of the drug delivery system. In one embodiment the drug delivery system can release between 10 ng and about 200 µg of an anti-neovascular agent (such as bevacizumab) over a 24 hour period after intraocular injection of implantation of the drug delivery system.

A detailed method within the scope of our invention is a method for treating dry AMD in a patient with dry AMD in one eye and wet AMD in the other eye, the method comprising the step of injecting a biocompatible drug delivery system comprising an anti-neovascular agent and a polymeric vehicle associated with the anti-neovascular agent into the vitreous cavity of the dry AMD eye of the patient, thereby treating the dry AMD by preventing or by delaying the progression of the dry AMD to wet AMD in the treated eye.

A further detailed method within the scope of our invention is a low dose method for treating dry AMD, the method comprising the steps of: (a) preparing a biocompatible, sustained release drug delivery system comprising between about 5 µg and about 20 µg bevacizumab and a polymeric hyaluronic acid vehicle associated with the bevacizumab, (b) injecting the drug delivery system into the vitreous cavity of the eye of a patient with dry AMD, and; (c) releasing from the drug delivery system an average of between about 14 nanograms to about 120 nanograms of the bevacizumab over a 24 hour period over a period of time of about 1 month or more, or for about 2 months or for about 3 months or more (preferably, the drug delivery system can release the active agent for between about 3 months and about 6 months), thereby treating the dry AMD with low doses of the bevacizumab released from the drug delivery system. The other, non-injected eye of the patient can have wet AMD and the dry AMD is treated by preventing or delaying onset of retinal neovascularization in the dry AMD eye injected.

The drug delivery system can have a viscosity of between about 130,000 cps and about 300,000 cps at a shear rate of about 0.1/second at about 25° C. and the drug delivery system can injected through a 25 to 30 gauge syringe.

Our invention also encompasses a low dose method for treating dry AMD, the method comprising the steps of: (a) preparing a biocompatible, sustained release drug delivery system comprising between about 5 µg and about 20 µg bevacizumab and a polymeric hyaluronic acid vehicle associated with the bevacizumab, (b) using a 25 to 30 gauge syringe injecting the drug delivery system into the vitreous cavity of the eye of a patient with dry AMD, wherein the other, non-injected eye of the patient has wet AMD, and; (c) releasing from the drug delivery system an average of between about 14 nanograms to about 120 nanograms of the bevacizumab over a 24 hour period over a period of time between about 3 months and about 6 months, thereby treating the dry AMD with low doses of the bevacizumab released from the drug delivery system by preventing or delaying onset of retinal neovascularization in the dry AMD eye injected, wherein the drug delivery system has a viscosity of between about 130,000 cps and about 300,000 cps at a shear rate of about 0.1/second at about 25° C.

A further method within the scope of our invention is a method for preventing development of choroidal neovascularization, the method comprising the steps of: (a) preparing a biocompatible drug delivery system comprising an anti-neovascular drug and a polymeric hyaluronic acid associated with the anti-neovascular drug, and; (b) injecting the drug delivery system into an intraocular location (such as a sub-tenon, subconjunctival, suprachoroidal, intrascleral, intravitreal or retrobulbar intraocular location) thereby preventing the development of the choroidal neovascularization. The polymeric hyaluronic acid used can be a cross-linked hyaluronic acid or a noncross-linked hyaluronic acid or mixtures thereof and preferably, the polymeric hyaluronic acid has a molecular weight between about 1 million Daltons and about 2 million Daltons.

To summarize, our invention encompasses compositions and method for treating an ocular condition by preparing a biocompatible drug delivery system comprising a drug and a polymeric vehicle for the drug, and injecting or implanting the drug delivery system into an intraocular location. The polymeric vehicle can be for example a collagen, a polysaccharide (such as a hydroxypropylmethylcellulose, alginate, chitosan, agar and pectin), a hyaluronic acid or a biodegradable polymer, such as a PLGA or a PLA polymer. The intraocular location can be an anterior or posterior intraocular location and the ocular condition can be an anterior or posterior ocular condition. The intraocular location can be a sub-tenon, subconjunctival, suprachoroidal, intrascleral, intravitreal or retrobulbar intraocular locations.

DRAWING

FIG. 1 is a graph showing percent viability (Y axis) in vitro of the retinal pigment epithelial cells ARPE-19 (y-axis 100% viability is the viability of the ARPE-19 cells at time zero) after 24, 48 and 72 hour periods of incubation in vitro in the concentrations of polysorbate 80 shown on the X axis.

DESCRIPTION

Our invention is based on the discovery than an anti-neovascular agent can be used to treat a condition, such as dry AMD, even when no neovascularization is present in the dry AMD eye of the patient to be treated. Prior to our invention it was not known that an anti-neovascular agent could be used to treat a condition, such as dry AMD, where no neovascularization is present in the eye of the patient to be treated. See eg Lin J., et al., *Vascular Endothelial Growth Factor Gene Polymorphisms in Age-related Macular Degeneration*, Am J Opthalmol. 2008 Mar. 29(VEGF gene not associated with dry AMD patient DNA, and; Cook H., et al., *Age-related macular degeneration: diagnosis and management*, BR Med Bull. 2008;85:127-49(". . . there is no treatment for advanced dry AMD . . . "). Our invention treats dry AMD by preventing or by delaying progression of the dry AMD to wet AMD.

Without wishing to be bound by theory we can postulate a mechanism for the effectiveness of our invention and embodiments therein. Thus, it can be estimated that a patient with wet AMD in one eye has a 10% chance (each year) of developing neovascularization (wet AMD) in the other eye. These percentages are cummulative so that over 5 years the patient with one wet AMD in one eye has a 50% chance of developing wet AMD in the other eye, possibly due to the presence of mutation in the complement factor H gene. We believe that genetically mediated processes which led to development of wet AMD in one eye will over time prevail n the other eye, so that such patients are at high-risk for developing wet (neovascular) AMD in both eyes and preventative measures are therefore indicated to reduce the chance of the patient developing severe vision loss in both eyes.

Hence, we postulate that anti-neovascular therapy can be effective to treat dry AMD, to thereby prevent it's progression to wet AMD, even though the dry AMD eye to be treated has little or no neovascularization. To reduce the chance of progressing from dry to wet AMD, relevant targets include the vascular endothelial growth factor (VEGF) pathway. VEGF is an important signaling protein involved in both vasculogenesis and angiogenesis. In patients with dry AMD, an overexpression of VEGF has been implicated in the progression to CNV. VEGF has been validated as an important target since VEGF-blockers, such as Macugen™ (pegaptanib), a pegylated aptamer that specific blocks VEGF165, and more importantly, Avastin™ (bevacizumab), a monoclonal antibody which is more promiscuous and blocks all known VEGF isoforms VEGF121, VEGF165, VEGF189, and VEGF20. VEGF blockers have been used extensively for CNV associated with AMD, proliferative diabetic retinopathy (PDR), neovascular glaucoma, diabetic macular edema (DME), and macular edema secondary to retinal vein occlusion (RVO). Results with anti-VEGF blockade are most impressive for CNV associated with AMD.

Although not currently approved by the FDA for such use, the injection of 1.25 to 2.5 mg of aqueous (i.e. immediate release) bevacizumab (i.e. not as a sustained or extended release drug delivery system) into the vitreous cavity has been performed without significant intraocular toxicity noted in both animal and human studies. The vitreous half-life of an anti-VEGF monoclonal antibody, such as bevacizumab, after injection into the vitreous from an immediate release (i.e. aqueous) formulation is only 5 to 6 days. Immediate release anti-neovascular formulations therefore cannot provide any ongoing or prolonged therapeutic effect (due to the immediate, one-time release) and require frequent, painful re-injection to treat an ocular condition.

Thus, although intravitreal aqueous formulation bevacizumab doses as high as 1.25 to 2.5 mg have been administered to treat macular neovascularization (wet AMD) we believe it is possible that bevacizumab doses less than 1% of known intravitreal dosages (i.e. less than 12 µg) can suppress neovascularization. We postulate that a dose of bevacizumab as low as 6.2 ug (i.e. as little as 0.5% of the known 1.25 mg dose) can be used to treat or to prevent intraocular neovascularization in humans (i.e. to treat dry AMD). Thus, 1.25 mg to 2.5 mg of an anti-neovascular agent, such as bevacizumab, can be released into the vitreous over a 3-6-month period from a sustained release drug delivery system to provide long term treatment of a chronic ocular condition such as dry AMD.

A hydrogel is a colloidal gel formed as a dispersion in water or other aqueous medium. Thus a hydrogel is formed upon formation of a colloid in which a dispersed phase (the polymer) has combined with a continuous phase (i.e. water) to produce a viscous jellylike product; for example, coagulated silicic acid. A hydrogel is a three-dimensional network of hydrophilic polymer chains that are crosslinked through either chemical or physical bonding. Because of the hydrophilic nature of the polymer chains, hydrogels absorb water and swell (unless they have already absorbed their maximum amount of water). The swelling process is the same as the dissolution of non-crosslinked hydrophilic polymers. By definition, water constitutes at least 10% of the total weight (or volume) of a hydrogel.

Examples of hydrogels include synthetic polymers such as polyhydroxy ethyl methacrylate, and chemically or physically crosslinked polyvinyl alcohol, polyacrylamide, poly(N-vinyl pyrolidone), polyethylene oxide, and hydrolysed polyacrylonitrile. Examples of hydrogels which are organic polymers include covalent or ionically crosslinked polysaccharide-based hydrogels such as the polyvalent metal salts of alginate, pectin, carboxymethyl cellulose, heparin, hyaluronate and hydrogels from chitin, chitosan, pullulan, gellan and xanthan. The particular hydrogels used in our experiment were a cellulose compound (i.e. hydroxypropylmethylcellulose [HPMC]) and a high molecular weight hyaluronic acid (HA).

As an embodiment of our invention we made a hydrogel formulation for intravitreal injection using a polymeric hyaluronic acid and an anti-VEGF monoclonal antibody. This drug delivery system can provide sustained-release of a low daily dose of the anti-VEGF monoclonal antibody over a 3 to 6 month period and prevent of conversion from dry to wet AMD. The drug delivery system can also comprise microsphere encapsulation of the anti-VEGF antibody in the hydrogel. The sustained-release drug delivery system can provide the necessary anti-VEGF blockade in eye to reduce the chance of progression from dry to neovascular AMD. In addition, the low doses released in the eye over a prolonged period of time do not provide a systemic toxic level of the anti-neovascular agent.

Our sustained release drug delivery system can also be used to provide sustained-release anti-VEGF blockade in patients with central retinal vein occlusion that are at risk for neovascularization and in patients with severe non-proliferative diabetic retinopathy that are at risk of progressing to neovascular disease.

Alternately, the drug delivery system can be a PLGA implant, liposomal encapsulated antibodies optionally entrapped in a cross-linked hyaluronic acid. Additionally, microspheres, microcapsules (ranging from 0.001 to 100 microns) and liposomes with modified surfaces to create an interaction with the hydrogel polymer to modify release. Other anti-VEGF compounds can be used in place of an anti-VEGF monoclonal antibody (e.g. bevacizumab) and these include anti-VEGF aptamers (e.g. pegaptanib), soluble recombinant decoy receptors (e.g. VEGF Trap), antibody fragments (e.g. ranibizumab), corticosteroids, small interfering RNA's decreasing expression of VEGFR or VEGF ligand, post-VEGFR blockade with tyrosine kinase inhibitors, MMP inhibitors, IGFBP3, SDF-1 blockers, PEDF, gamma-secretase, Delta-like ligand 4, integrin antagonists, HIF-1 alpha blockade, protein kinase CK2 blockade, and inhibition of stem cell (i.e. endothelial progenitor cell) homing to the site of neovascularization using vascular endothelial cadherin (CD-144) and stromal derived factor (SDF)-1 antibodies. Agents that have activity against CNV that are not necessarily anti-VEGF compounds can also be used and include anti-inflammatory drugs, rapamycin, cyclosporine, anti-TNF agents, and anti-complement agents.

Our invention also encompasses particular drug delivery system formulations and methods for administering these drug delivery systems for treating an ocular condition, such as dry AMD. The present invention encompasses drug delivery systems which are structured and configured solely for intraocular, as opposed to topical or systemic, administration. The intraocular administration can be by implantation or injection into the vitreous cavity (posterior chamber) of the eye. The drug delivery systems within the scope of our invention can be biodegradable implants and/or microspheres. The drug delivery systems can be monolithic, that is the active agent is homogenously distributed or dispersed throughout the biodegradable polymer. The therapeutic agent can be released from drug delivery systems made according to the present invention for a period of time between about 2 hours to 12 months or more. An important feature of our drug delivery systems is that they do not include any means (such as a cap, protrusion or suture tab) for fixing the drug delivery system to the intraocular location to which it is administered.

An important characteristic of a drug delivery system within the scope of our invention is that it can be implanted or injected into an intraocular location (such as an anterior sub-Tenon, subconjunctival, intravitreal or suprachoroidal location) to provide sustained release of a therapeutic agent without the occurrence of or the persistence of significant immunogenicity at and adjacent to the site of the intraocular implantation or injection.

Polylactide (PLA) polymers exist in 2 chemical forms, poly(L-lactide) and poly(D,L-lactide). The pure poly(L-lactide) is regioregular and therefore is also highly crystalline, therefore degrades in vivo at a very slow rate. The poly(D,L-lactide) is regiorandom which leads to more rapid degradation in vivo. Therefore a PLA polymer which is a mixture of predominantly poly(L-lactide) polymer, the remainder being a poly(D-lactide) polymer will degrade in vivo at a rate slower that a PLA polymer which is predominantly poly(D-lactide) polymer. A PLGA is a co-polymer that combines poly(D,L-lactide) with poly(glycolide) in various possible ratios. The higher the glycolide content in a PLGA the faster the polymer degradation.

In one embodiment of our invention, a drug delivery system for intraocular administration (i.e. by intravitreal implantation or injection) comprises configured, consists of, or consists essentially of at least a 75 weight percent of a PLA and no more than about a 25 weight percent of a poly(D,L-lactide-co-glycolide) polymer.

Within the scope of our invention are suspensions of microspheres (incorporating an anti-neovascular agent) suspended in a hydrogel (such as a polymeric hyaluronic acid) which can be administered to an intraocular location through a syringe needle. Administration of such a suspension requires that the viscosity of the microsphere suspension at 25° C. be less than about 300,000 cP. The viscosity of water at 25° C. is about 1. cP (cP or cps is centiposie, a measure of viscosity). At 25° C. the viscosity of olive oil is 84 cP, of castor oil 986 P and of glycerol 1490 cP The drug delivery systems of our invention can include a therapeutic agent mixed with or dispersed within a biodegradable polymer. The drug delivery systems compositions can vary according to the preferred drug release profile, the particular active agent used, the ocular condition being treated, and the medical history of the patient. Therapeutic agents which can be used in our drug delivery systems include, but are not limited to (either by itself in a drug delivery system within the scope of the present invention or in combination with another therapeutic agent): ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites, antiangiogenic agents, tyrosine kinase inhibitors, antibiotics such as aminoglycosides such as gentamycin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline; quinolones such as ciprofloxin, etc.; sulfonamides such as chloramine T; and sulfones such as sulfanilic acid as the hydrophilic entity, anti-viral drugs, e.g. acyclovir, gancyclovir, vidarabine, azidothymidine, azathioprine, dideoxyinosine, dideoxycytosine, dexamethasone, ciprofloxin, water soluble antibiotics, such as acyclovir, gancyclovir, vidarabine, azidothymidine, dideoxyinosine, dideoxycytosine; epinephrine; isoflurphate; adriamycin; bleomycin; mitomycin; ara-C; actinomycin D; scopolamine; and the like, analgesics, such as codeine, morphine, keterolac, naproxen, etc., an anesthetic, e.g. lidocaine; beta.-adrenergic blocker or beta.-adrenergic agonist, e.g. ephidrine, epinephrine, etc.; aldose reductase inhibitor, e.g. epairestat, ponalrestat, sorbinil, tolrestat; antiallergic, e.g. cromolyn, beclomethasone, dexamethasone, and flunisolide; colchicine, anihelminthic agents, e.g. ivermectin and suramin sodium; antiamebic agents, e.g. chloroquine and chlortetracycline; and antifungal agents, e.g. amphotericin, etc., anti-angiogenesis compounds such as anecortave acetate, retinoids such as Tazarotene, anti-glaucoma agents, such as brimonidine (Alphagan and Alphagan P), acetozolamide, bimatoprost (Lumigan), timolol, mebefunolol; memantine, latanoprost (Xalatan); alpha-2 adrenergic receptor agonists; 2-methoxyestradiol; anti-neoplastics, such as vinblastine, vincristine, interferons; alpha, beta and gamma, antimetabolites, such as folic acid analogs, purine analogs, and pyrimidine analogs; immunosuppressants such as azathiprine, cyclosporine and mizoribine; miotic agents, such as carbachol, mydriatic agents such as atropine, protease inhibitors such as aprotinin, camostat, gabexate, vasodilators such as bradykinin, and various growth factors, such epidermal growth factor, basic fibroblast growth factor, nerve growth factors, carbonic anhydrase inhibitors, and the like.

In particular embodiments of our invention, the active agent can be a compound that blocks or reduces the expression of VEGF receptors (VEGFR) or VEGF ligand including but not limited to anti-VEGF aptamers (e.g. Pegaptanib), soluble recombinant decoy receptors (e.g. VEGF Trap), anti-VEGF monoclonal antibodies (e.g. Bevacizamab) and/or antibody fragments (e.g. Ranibizamab), small interfering RNA's decreasing expression of VEGFR or VEGF ligand, post-VEGFR blockade with tyrosine kinase inhibitors, MMP inhibitors, IGFBP3, SDF-1 blockers, PEDF, gamma-secretase, Delta-like ligand 4, integrin antagonists, HIF-1 alpha blockade, protein kinase CK2 blockade, and inhibition of stem cell (i.e. endothelial progenitor cell) homing to the site of neovascularization using vascular endothelial cadherin (CD-144) and stromal derived factor (SDF)-1 antibodies.

In another embodiment or variation of our invention the active agent is methotrexate. In another variation, the active agent is a retinoic acid. In another variation, the active agent is an anti-inflammatory agent such as a nonsteroidal anti-inflammatory agent. Nonsteroidal anti-inflammatory agents that may be used include, but are not limited to, aspirin, diclofenac, flurbiprofen, ibuprofen, ketorolac, naproxen, and suprofen. In a further variation, the anti-inflammatory agent is a steroidal anti-inflammatory agent, such as dexamethasone.

Steroidal anti-inflammatory agents that can be used in our drug delivery systems can include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and any of their derivatives.

In one embodiment, cortisone, dexamethasone, fluocinolone, hydrocortisone, methylprednisolone, prednisolone, prednisone, and triamcinolone, and their derivatives, are preferred steroidal anti-inflammatory agents. In another preferred variation, the steroidal anti-inflammatory agent is dexamethasone. In another variation, the biodegradable implant includes a combination of two or more steroidal anti-inflammatory agents.

The active agent, such as an anti-neovascular agent, can comprise from about 1% to about 90% by weight of the implant or drug delivery system. In one variation, the agent is from about 5% to about 80% by weight of the implant. In a preferred variation, the agent comprises from about 10% to about 60% by weight of the implant. In a more preferred embodiment of the present invention, the agent can comprise about 50% by weight of the implant.

The therapeutic active agent present in our drug delivery systems can be homogeneously dispersed in the biodegradable polymer of the drug delivery system. The selection of the biodegradable polymer used can vary with the desired release kinetics, patient tolerance, the nature of the disease to be treated, and the like. Polymer characteristics that are considered include, but are not limited to, the biocompatibility and biodegradability at the site of implantation, compatibility with the active agent of interest, and processing temperatures. The biodegradable polymer matrix usually comprises at least about 10, at least about 20, at least about 30, at least about 40, at least about 50, at least about 60, at least about 70, at least about 80, or at least about 90 weight percent of the implant. In one variation, the biodegradable polymer matrix comprises about 40% to 50% by weight of the drug delivery system.

Biodegradable polymers which can be used include, but are not limited to, polymers made of monomers such as organic esters or ethers, which when degraded result in physiologically acceptable degradation products. Anhydrides, amides, orthoesters, or the like, by themselves or in combination with other monomers, may also be used. The polymers are generally condensation polymers. The polymers can be crosslinked or non-crosslinked.

For the most part, besides carbon and hydrogen, the polymers will include oxygen and nitrogen, particularly oxygen. The oxygen may be present as oxy, e.g., hydroxy or ether, carbonyl, e.g., non-oxo-carbonyl, such as carboxylic acid ester, and the like. The nitrogen can be present as amide, cyano, and amino. An exemplary list of biodegradable polymers that can be used are described in Heller, *Biodegradable Polymers in Controlled Drug Delivery*, In: "CRC Critical Reviews in Therapeutic Drug Carrier Systems", Vol. 1. CRC Press, Boca Raton, Fla. (1987).

Of particular interest are polymers of hydroxyaliphatic carboxylic acids, either homo- or copolymers, and polysaccharides. Included among the polyesters of interest are homo- or copolymers of D-lactic acid, L-lactic acid, racemic lactic acid, glycolic acid, caprolactone, and combinations thereof. Copolymers of glycolic and lactic acid are of particular interest, where the rate of biodegradation is controlled by the ratio of glycolic to lactic acid. The percent of each monomer in poly(lactic-co-glycolic)acid (PLGA) copolymer may be 0-100%, about 15-85%, about 25-75%, or about 35-65%. In certain variations, 25/75 PLGA and/or 50/50 PLGA copolymers are used. In other variations, PLGA copolymers are used in conjunction with polylactide polymers.

Other agents may be employed in a drug delivery system formulation for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA for the desired route of administration. Surfactants which can be used to stabilize particles in a colloid and/or electrolytes such as sodium chloride and potassium chloride can also be included in the formulation. The drug delivery system can also acid and basic excipients to control pH in the microenvironment as well as at interfaces (diffusional stagnant layer).

The biodegradable drug delivery systems can also include additional hydrophilic or hydrophobic compounds that accelerate or retard release of the active agent. Additionally, release modulators such as those described in U.S. Pat. No. 5,869,079 can be included in the implants. The amount of release modulator employed will be dependent on the desired release profile, the activity of the modulator, and on the release profile of the glucocorticoid in the absence of modulator. Where the buffering agent or release enhancer or modulator is hydrophilic, it may also act as a release accelerator. Hydrophilic additives act to increase the release rates through faster dissolution of the material surrounding the drug particles, which increases the surface area of the drug exposed, thereby increasing the rate of drug diffusion. Similarly, a hydrophobic buffering agent or enhancer or modulator can dissolve more slowly, slowing the exposure of drug particles, and thereby slowing the rate of drug diffusion.

A drug delivery system within the scope of the present invention can be formulated with particles of an active agent dispersed within a biodegradable polymer. Without being bound by theory, it is believed that the release of the active agent can be achieved by erosion of the biodegradable polymer matrix and by diffusion of the particulate agent into an ocular fluid, e.g., the vitreous, with subsequent dissolution of the polymer matrix and release of the active agent. Factors which influence the release kinetics of active agent from the implant can include such characteristics as the size and shape of the implant, the size of the active agent particles, the solubility of the active agent, the ratio of active agent to polymer(s), the method of manufacture, the surface area exposed, the density of the implant and the erosion rate of the polymer(s).

The release rate of the active agent can depend at least in part on the rate of degradation of the polymer backbone component or components making up the biodegradable polymer matrix. For example, condensation polymers may be degraded by hydrolysis (among other mechanisms) and therefore any change in the composition of the implant that enhances water uptake by the implant will likely increase the rate of hydrolysis, thereby increasing the rate of polymer degradation and erosion, and thus increasing the rate of active agent release. The release rate of the active agent can also be influenced by the crystallinity of the active agent, the pH in the implant and the pH at interfaces.

The release kinetics of the drug delivery systems of the present invention can be dependent in part on the surface area of the drug delivery systems. A larger surface area exposes more polymer and active agent to ocular fluid, causing faster erosion of the polymer and dissolution of the active agent particles in the fluid.

Examples of ocular conditions which can be treated by the drug delivery systems and methods of the invention include, but are not limited to, glaucoma, uveitis, macular edema, macular degeneration, retinal detachment, posterior ocular tumors, fungal or viral infections, multifocal choroiditis, diabetic retinopathy, proliferative vitreoretinopathy (PVR), sympathetic opthalmia, Vogt Koyanagi-Harada (VKH) syndrome, histoplasmosis, uveal diffusion, and vascular occlusion. In one variation, the implants are particularly useful in treating such medical conditions as uveitis, macular edema, vascular occlusive conditions, proliferative vitreoretinopathy (PVR), and various other retinopathies.

The drug delivery systems of our invention can be injected to an intraocular location by syringe or can be inserted (implanted) into the eye by a variety of methods, including placement by forceps, by trocar, or by other types of applicators, after making an incision in the sclera. In some instances, a trocar or applicator may be used without creating an incision. In a preferred variation, a hand held applicator is used to insert one or more biodegradable implants into the eye. The hand held applicator typically comprises an 18-30 GA stainless steel needle, a lever, an actuator, and a plunger. Suitable devices for inserting an implant or implants into a posterior ocular region or site includes those disclosed in U.S. patent application Ser. No. 10/666,872.

The method of administration generally first involves accessing the target area within the ocular region with the needle, trocar or implantation device. Once within the target area, e.g., the vitreous cavity, a lever on a hand held device can be depressed to cause an actuator to drive a plunger forward. As the plunger moves forward, it can push the implant or implants into the target area (i.e. the vitreous).

Various techniques may be employed to make implants within the scope of the present invention. Useful techniques include phase separation methods, interfacial methods, extrusion methods, compression methods, molding methods, injection molding methods, heat press methods and the like.

The drug delivery systems disclosed herein can be used to prevent or to treat various ocular diseases or conditions, including the following: maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

EXAMPLES

The following examples illustrate aspects and embodiments of our invention.

Example 1

Intravitreal Bevacizumab-PLGA Microspheres for Treatment of Dry AMD

A 78 year old man has age-related macular degeneration and cataracts in both eyes. The patient can also have a history of cardiovascular disease and an inferior wall myocardial infarction 6 months previous. The patient can complain of blurry vision and metamorphopsia in the right eye and examination can reveal visual acuity of 20/400 right eye, 20/32 left eye. Retinal examination can show subfoveal choroidal neovascularization (CNV) (right eye wet AMD) approximately 1 disc area in size with surrounding hemorrhage and edema in the right eye. The fellow left eye can show high-risk features for developing wet AMD such as soft, amorphic appearing drusen that included the fovea but no signs of choroidal neovascularization and can be confirmed by fluorescein angiography (left eye dry AMD). The patient can be started on monthly intravitreal injections of ranibizumab (an anti-neovascular agent) in the right wet AMD eye with resolution of the edema and hemorrhage and a return in visual acuity to 20/125 within 4 months.

In the left eye, the patient can receive an intravitreal injection of a sustained-release anti-VEGF monoclonal antibody formulation (optionally with a penetration enhancer) to prophylax against development of CNV in this eye given that he is now at high risk for developing wet AMD in the better seeing left eye. The injected volume can be 50 ul comprising bevacizumab incorporated into PLGA microspheres with a total bevacizumab (drug) weight of 2.5 mg.

Polysorbate 20 PLGA microspheres with an in vitro release rate of 10 ug/day can also be placed in the formulation to enhance retinal permeability. The bevacizumab and polysorbate 20 microspheres are placed in a cross-linked hyaluronic acid at a concentration of 1.2% with reasonable syringability using a 27 G needle.

The patient can receive the intravitreal left eye injections of the 50 ul of bevacizumab-PLGA microspheres (total drug weight 2.5 mg) invention every 6 months and at the end of a 7-year follow up period the patient can have maintained vision in the left eye at 20/32. His risk of having developed wet AMD in this left eye was over 50% but repeat examination can reveal no signs of CNV in the left eye. Unfortunately, at the end of the 7 year follow up, the vision in the right eye can have deteriorated to 20/400 with an organized disciform scar present on examination in the central macular area. Given that he does not lose vision in the left eye, he is able to maintain a driver's license and an independent life style over this time frame. Despite have been exposed to sustained-low dose anti-VEGF therapy in the eye, the patient's cardiovascular disease can remain unchanged without experience of any thromboembolic events.

The microspheres used therapeutically in Examples 1 to 3 can be made by a solvent evaporation method from methylene chloride into a PVA (polyvinyl alcohol) solution. From 10 to 100 mg/mL of the microspheres can be suspended in an isotonic phosphate buffer solution and from 50 to 200 µL of the microsphere suspension can be administered to an intraocular location.

The anti-neovascular agent microspheres with the anti-neovascular agent homogenously distributed or dispersed throughout the selected polylactic acid (PLA) or PLGA resin can be manufactured using an emulsion/solvent evaporation technique. The non-solvent (continuous aqueous phase) is saturated with the anti-neovascular agent to prevent loss of the anti-neovascular agent from the polymer phase and increase loading efficiency. Additionally, the anti-neovascular agent saturated with methanol can be used to quench the emulsion. The methanol served as a sink to remove the dichloromethane quickly, hardening the microspheres before the anti-neovascular agent can diffuse out of them.

Example 2

Low Dose Intravitreal Bevacizumab-PLGA Microspheres for Treatment of Dry AMD

A 74 year old man is diagnosed with dry age-AMD in one (right) eye and wet AMD in the other (left) eye. He has 20/40 vision in his right eye. He is treated by intravitreal injection into the dry AMD eye of a sustained release drug delivery system. Sustained release drug delivery system comprises a total of about 6 micrograms (low dose) of the active agent bevacizumab in a polymeric vehicle. The polymeric vehicle is a high viscosity hyaluronic acid or a PLGA or PLA associated with the bevacizumab anti-neovascular agent to form either a plurality of microspheres or a single monolithic implant in which the bevacizumab is homogenously distributed. Alternately the sustained release drug delivery system can comprise the bevacizumab microspheres or implant in the hyaluronic acid (cross-linked or non-cross linked), so that both a viscous (the hyaluronic acid) and the solid (the PLA or PLGA microspheres or implant) polymeric vehicles are present in the same drug delivery system. The drug delivery system can release the 6 µg of bevacizumab into the vitreous over a 1 to 6 month period, after which the patient's right eye can show no evidence of neovascularization and the same vision maintained (20/40) in his right eye.

Example 3

Intravitreal Ranibizumab-PLGA Microspheres for Treatment of Dry AMD

An 83 year old woman can wake up with blurry vision in the left eye. She can have a history of glaucoma, s/p cataract removal with IOLs (intraocular lenses), and dry AMD in both eyes and can be taking Alphagan P eye drops. The patient's ophthalmologist can examine her and she can be diagnosed with left eye wet AMD and sent immediately to a retinal specialist. The vision can be 20/25 in the right eye and 20/200 in the left eye. Retinal examination can show dry changes in the right eye macula but high risk features such as large drusen and numerous pigmentary changes in the subfoveal region. The left eye macula can show a subfoveal CNV approximately 2 disc areas in size with surrounding macular edema and intraretinal hemorrhages. Fluorescein angiography can confirm the presence of left eye CNV predominantly classic in appearance. The patient can be immediately started on monthly intravitreal injections of ranibizumab in the wet AMD left eye with resolution of the retinal edema over a 3 month period but she can experience only a modest improvement of left eye visual acuity to 20/100. Since the patient was at high risk for developing CNV in her right eye, and the vision in the left eye may not appreciably improve over the 3 month period, she can receive an intravitreal injection into the right eye of 50 ul comprising 4.8 mg of ranibizumab incorporated into PLGA microspheres, to prophylax against the development of CNV in the right eye. Polysorbate 20 PLGA microspheres with an in vitro release rate of 5 ug/day can also be placed in the formulation to enhance retinal permeability. The microspheres can be placed in a partially cross-linked hyaluronic acid (HA) at a HA concentration of 2.1%. Such a cross-linked HA can be obtained from Allergan Medical (Irvine, Calif.) under the brand names Juvederm Ultra Plus, Juvederm 30, Captique, and Voluma.

She can have repeat right eye intravitreal injections of the 50 ul comprising 4.8 mg of ranibizumab-PLGA microspheres every 6 months over a 4 year period with visual acuity remaining 20/25 in the right eye and 20/200 for the left eye. Retinal examination can show dry AMD in the right eye and an organized disciform scar in the left eye with mild subfoveal fibrosis. She can be able to live independently in her own home given the excellent vision that she can maintain in her right eye.

Example 4

Anti-Neovascular Drug Delivery System with a Retinal Penetration Enhancer

An experiment was carried out to examine the toxicity of a polysorbate retinal penetrant enhancer to retinal pigment epithelial ("RPE") cells. Thus, ARPE-19 cells (see Dunn K. et al., *ARPE-19, a human retinal pigment epithelial cell line with differentiated properties*, Exp Eye Res. February 1992; 62(2):155-69) were incubated in vitro in concentrations of polysorbate 80 ranging from 0% to 0.10% w/w and a cell viability assay was performed.

The protocol for this in vitro experiment was as follows: ARPE-19 cells (passage 11 to 23) were seeded the day prior to experimentation in 24 well-plates at 125.000 cells/well in DMEM:F12 medium supplemented with 10% FBS. Time course and dose response were simultaneously performed on ARPE-19 cells. Parameters of incubating solutions such as pH, osmolarity were measured for every concentration. Times of incubation were 24 h, 48 h, 72 h. One negative (non-treated) and one positive control (5 mM $H_2O_2$) were included. Non-treated condition was cell culture medium supplemented with serum. 5 mM $H_2O_2$ was prepared from 3% $H_2O_2$ stock solution (875 mM). Concentrations applied to cells were determined considering several parameters, such as:

(a) commonly used concentration in formulation.
(b) limiting concentration to compound solubility.
(c) limiting concentration to applicable viscosity, osmolarity and pH values.

In a first approach, the concentrations covered a wide range (Exp. 1). After preliminary results, a second set of experiments (Exp. 2 to 4) determined more accurately compound concentrations leading to inhibition of 50% of cell viability, based on cell viability assay and morphological aspect. All range of concentrations were obtained with serial dilution from most the concentrated condition into cell culture medium (DMEM:F12 supplemented with 10% FBS). Results from MTT assay were expressed as a percentage of cell viability calculated as follows:

% cell viability=$OD$test/$OD$control×100.

After 3 experiments were independently completed in the same conditions, a graph was plotted from 3 sets of values, yielding to inter-experimental standard variation values. Gap concentration bringing to 50% cell viability was therefore determined. Morphological appearance was analyzed by semi-quantitative scoring ranging from 5 to 1, from normal to lethal phenotype respectively.

It was observed that polysorbate 80 concentrations over about 0.06% (0.6 mg/ml) were associated with declining RPE cell viability, and polysorbate 80 concentrations greater than about approximately 0.09% (0.9 mg/ml) were associated with cell viabilities of less than 50%, as shown by FIG. 1. Assuming a vitreous volume of 4 ml in a human eye, the total maximum weight of polysorbate in the vitreous at one time therefore should not exceed 3.6 mg.

In each of Examples 1-3 above one or more retinal penetration enhancers can be included in the drug delivery system to increase the permeability of the retina to the anti-neovascular agent used. Thus, a retinal penetration enhancers can be added to the sustained release drug delivery system to release concomitantly with the anti-neovascular agent (i.e. an anti-VEGF compound). Co-releasing both a low dose of anti-VEGF compound and a penetration enhancer over a 6 month period can optimize the efficiency of the anti-VEGF compounds especially the larger ones such as a monoclonal antibody, to reach the sub-retinal space to treat CNV. A preferred retinal penetrant enhancer is polysorbate 20 (eg Tween 20 or C12-sorbitan-E20) and polysorbate 80, added to the drug delivery system as an aqueous solution with a concentration of the retinal penetration enhancer in the aqueous solution of between about from 0.005% to 0.10% (0.05 mg to 1 mg of the retinal penetration enhancer per ml water. Alternative retinal penetration enhancers include but are not limited to sodium laurylsulfate, benzalkonium chloride, and cyclodextrans.

All references, articles, patents, applications and publications set forth above are incorporated herein by reference in their entireties.

Accordingly, the spirit and scope of the following claims should not be limited to the descriptions of the preferred embodiments set forth above.

We claim:

1. A method for delaying the progression of dry age related macular degeneration ("dry AMD") to wet age related macular degeneration ("wet AMD") in a patient, the method comprising the steps of:
   (a) selecting a patient having dry AMD in a first eye and wet AMD in a second eye,
   (b) preparing a biocompatible, sustained release drug delivery system comprising between about 5 μg and about 20 μg bevacizumab and a polymeric hyaluronic acid vehicle;
   (c) injecting the drug delivery system into the vitreous cavity of the first eye of the patient, and;
   (d) releasing from the drug delivery system an average of between about 14 nanograms to about 120 nanograms of the bevacizumab over a 24 hour period for a period of time between about 3 months and about 6 months, thereby preventing the progression of the dry AMD to wet AMD with the bevacizumab released from the drug delivery system.

2. The method of claim 1, wherein the drug delivery system has a viscosity of between about 130,000 cps and about 300,000 cps at a shear rate of about 0.1 second at about 25° C.

3. The method of claim 1, wherein the drug delivery system is injected using a 25 to 30 gauge syringe.

4. A method for delaying the progression of dry age related macular degeneration ("dry AMD") to wet age related macular degeneration ("wet AMD") in a patient, the method consisting essentially of:
   (a) preparing a biocompatible sustained release drug delivery system comprising between about 5 μg and about 20 μg bevacizumab and a polymeric hyaluronic acid vehicle,
   (b) using a 25 to 30 gauge syringe for injecting the drug delivery system into the vitreous cavity of the eye of a patient with dry AMD, wherein the other, non-injected eye of the patient has wet AMD, and;
   (c) releasing from the drug delivery system an average of between about 14nanograms to about 120 nanograms of the bevacizumab over a 24 hour period for a period of time between about 3 months and about 6 months, thereby treating the dry AMD and low doses of the bevacizumab released from the drug delivery system by preventing or delaying onset of retinal neovascularization in the dry AMD eye injected, wherein the drug delivery system has a viscosity of between about 130,000 cps and about 300,000 cps at a shear rate of about 0.1/second at about 25° C.

* * * * *